(12) United States Patent
Loomis et al.

(10) Patent No.: US 11,324,580 B2
(45) Date of Patent: May 10, 2022

(54) STERILE PACKAGING CONTAINER

(71) Applicant: NuVasive, Inc., San Diego, CA (US)

(72) Inventors: David Loomis, San Diego, CA (US);
Morton Albert, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 67 days.

(21) Appl. No.: 16/159,110

(22) Filed: Oct. 12, 2018

(65) Prior Publication Data

US 2020/0113666 A1 Apr. 16, 2020

Related U.S. Application Data

(63) Continuation of application No. PCT/US2017/027727, filed on Apr. 14, 2017.

(60) Provisional application No. 62/322,682, filed on Apr. 14, 2016.

(51) Int. Cl.
| | | |
|---|---|---|
| A61F 2/00 | (2006.01) | |
| A61L 2/08 | (2006.01) | |
| A61L 2/26 | (2006.01) | |
| A61L 2/20 | (2006.01) | |
| B29C 48/09 | (2019.01) | |
| B29L 31/00 | (2006.01) | |

(52) U.S. Cl.
CPC .......... *A61F 2/0095* (2013.01); *A61L 2/081* (2013.01); *A61L 2/206* (2013.01); *A61L 2/26* (2013.01); *A61L 2202/182* (2013.01); *A61L 2202/21* (2013.01); *B29C 48/09* (2019.02); *B29L 2031/712* (2013.01)

(58) Field of Classification Search
CPC ........ A61F 2/0095; A61L 2/081; A61L 2/206; A61L 2/26; A61L 2202/182; A61L 2202/21; B29C 48/09

USPC ................................... 206/438, 439
See application file for complete search history.

(56) References Cited

U.S. PATENT DOCUMENTS

| | | | | | |
|---|---|---|---|---|---|
| 5,071,766 A | * | 12/1991 | Barr | ........................ | C12M 23/08 |
| | | | | | 435/304.1 |
| 5,217,114 A | * | 6/1993 | Gadberry | ............. | A61M 25/002 |
| | | | | | 206/364 |
| 5,972,292 A | * | 10/1999 | DeMeo | ................. | A45C 11/005 |
| | | | | | 134/901 |
| 6,793,882 B1 | * | 9/2004 | Verschuur | ................ | B65D 1/32 |
| | | | | | 422/6 |

(Continued)

FOREIGN PATENT DOCUMENTS

| | | |
|---|---|---|
| JP | H0884773 | 7/2010 |
| WO | 2007078992 | 7/2007 |
| WO | 2012009653 | 1/2012 |

OTHER PUBLICATIONS

International Search Report for PCT/US17/27727, EP Search Authority, dated Nov. 23, 2017.

*Primary Examiner* — Jacob K Ackun
(74) *Attorney, Agent, or Firm* — Hoffman Warnick LLC

(57) ABSTRACT

The present disclosure in one aspect provides a sterile packaging container comprising a container body with a cross-sectional shape that is constant along the majority of the longitudinal axis, a cover and a closure assembly that inhibits the passage of microbial contaminants. The container is configured such that the interior of the container can be sterilized. The sterile packaging container described herein allows one to manufacture a sterile packaging tube exercising the smallest possible volume.

12 Claims, 11 Drawing Sheets

(56) References Cited

U.S. PATENT DOCUMENTS

| | | | | |
|---|---|---|---|---|
| 7,282,177 B2* | 10/2007 | Castaneda | ............... | A61B 7/02 |
| | | | | 283/56 |
| 7,624,868 B2* | 12/2009 | Booker | ............... | A61D 19/024 |
| | | | | 206/305 |
| 7,790,105 B2 | 9/2010 | Bala | | |
| 8,398,615 B2* | 3/2013 | Torstensen | .......... | A61M 25/002 |
| | | | | 604/544 |
| 8,851,286 B2* | 10/2014 | Chang | ................. | A61F 2/2427 |
| | | | | 206/464 |
| 2009/0008279 A1* | 1/2009 | Tanghoej | ............ | A61M 25/002 |
| | | | | 206/364 |
| 2014/0018742 A1 | 1/2014 | Sodhi | | |
| 2015/0367545 A1 | 12/2015 | Berg et al. | | |
| 2016/0001058 A1* | 1/2016 | Ziebol | ................... | A61L 29/08 |
| | | | | 604/265 |
| 2016/0051329 A1 | 2/2016 | Verschuur | | |

\* cited by examiner

STERILE PACKAGING CONTAINER

CROSS REFERENCE TO RELATED APPLICATIONS

This application claims priority to, and the benefit of, United States Provisional Patent Application No. 62/322,682 filed on Apr. 14, 2016. Provisional Patent Application No. 62/322,682 is incorporated herein by reference in its entirety.

FIELD OF INVENTION

The field of the invention generally relates to sterile packaging for maintaining the sterility of medical implants prior to implantation.

BACKGROUND

Maintaining the sterility of medical implants prior to implantation is of high importance during surgery to safeguard against infection. Currently this is accomplished using a variety of different methods. For example, implants are often housed and delivered, unsterilized, in large sterilization trays (together with the instruments used to facilitate their use) that are steam sterilized at the hospital just before surgery and delivered directly to the operating room. Implants used to replenish the trays are typically delivered in a disposable package that is discarded upon opening, the implant being placed in the tray for sterilization and eventual use.

Because the trays contain many implants (to account for various sizes, functions, etc.) many more implants are shipped to each case than are needed for any given procedure. This both increases shipping and inventory costs and subjects implants in the trays to repeated cycling through sterile and unsterile conditions. Alternatively, each of the implants may be individually packaged in some form of disposable packaging (e.g. plastic pouches or blister packs) that are opened directly in the operating room, with the packaging being discarded. These packages are generally effective at maintaining sterility of the implants within the package during storage and transport but can be a source of nuisance to handle and open within the operating room, as well as creating a lot of waste. Pressurized/vacuum vessels designed to hold individual implants have been utilized that are easier to handle, but conversely, can be a nuisance to transport and store as they are sensitive to temperature fluctuation.

More recently, sterile tubes, such as those described in U.S. Pat. No. 9,265,579, have been developed that have the sterility characteristics of the blister packs but are easier to handle and open in the operating room while also reducing overall waste. The tube includes at least a portion formed of, or covered, by a membrane that prevents the passage of bacteria but is permeable to gas. Similarly, gaps may be designed within the threading between the tube and associated caps allow gas passage at a similar particle level to Tyvek® paper, the current standard used in blister packs, to prevent the passage of bacteria. While such tubes are very effective, they are currently limited to use with smaller implants because of constraints in the manufacturing process. Specifically, the injection molding process used to create the tubes requires draft angle be imparted in the tube structure to allow the tube to be removed from the molding pieces. Thus, the length of the tube is directly tied to the diameter of the tube in that the larger length tube injection molded on z-axis is constrained by aspect ratio to correlate to a larger diameter as well.

SUMMARY

Disclosed herein is a sterile packaging container for maintaining the sterility of medical implants prior to implantation that is manufactured so that the length is irrespective to the diameter of the, which in turn, provides for the smallest possible volume for the container.

A sterile packaging container configured for sterilization and gas permeation is provided comprising a container body, a cover and a closure assembly. The container body has a longitudinal axis, a first open end, and a second open end, and the container body has a cross-sectional shape that is uniform along the majority of the length of the longitudinal axis. The cover and the closure assembly provide microbe-tight seals with the container body.

The sterile packaging container described herein may be placed within a second sterile packaging container. Such embodiments comprise a second sterile packaging container containing the sterile packaging container described above. This embodiment adds the additional feature of allowing the sterilization of the exterior of the first sterile packaging container.

A method of manufacturing a sterile packaging container via a mechanical process is provided, to create a polymeric container body having a first open end, a second open end, and a cross-sectional shape that is constant along the majority of its longitudinal axis. The container body is allowed to harden, and, the cover is hermetically sealed to the first open end of the container body. The closure base is subsequently hermetically sealed to the second open end of the container body. The removable closure cap is connected to the closure base, creating a gas permeable seal that inhibits microbial entry. Finally, the interior of the container body is sterilized.

An alternative embodiment of the method of manufacturing a sterile container is provided, comprising: extruding or pultruding a polymeric container body having a first open end, a second open end, and a cross-sectional shape that is constant along the majority of the longitudinal axis; allowing the container body to harden; sealing a cover to the first open end to create a first microbe-tight seal; sealing a closure to the second open end to create a second microbe-right seal; and sterilizing the interior of the container; wherein at least one of the first microbe-tight seal and the second microbe-tight seal is air permeable.

The foregoing presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Figure 1:
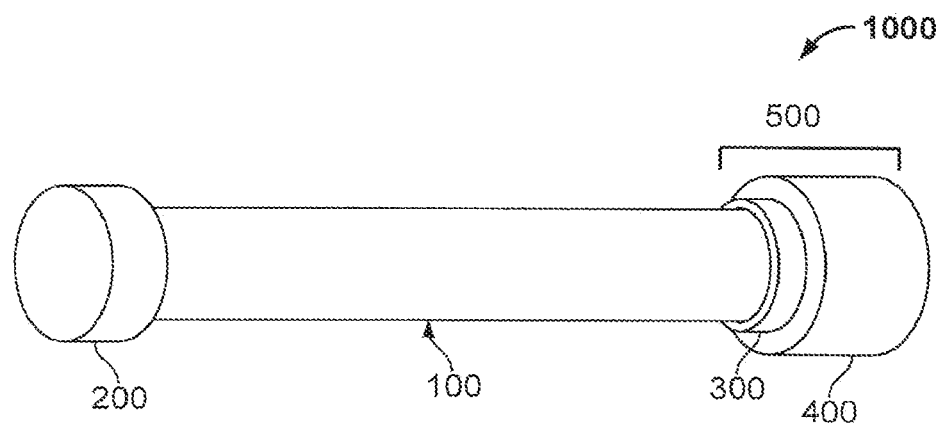
FIG. 1 illustrates an isometric view of an embodiment the sterile packaging container.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

While the subject matter is susceptible to various modifications and alternative forms, specific embodiments thereof have been shown by way of example in the drawings and are herein described in detail. It should be understood, however, that the description herein of specific embodiments is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

The present disclosure provides a sterile packaging container 1000 that allows for more flexibility in the manufacture of sterile packaging for implants. In the embodiment shown in in FIG. 1, the sterile packaging container 1000 comprises: a container body 100, a cover 200, and a closure assembly 500.

Figure 2:
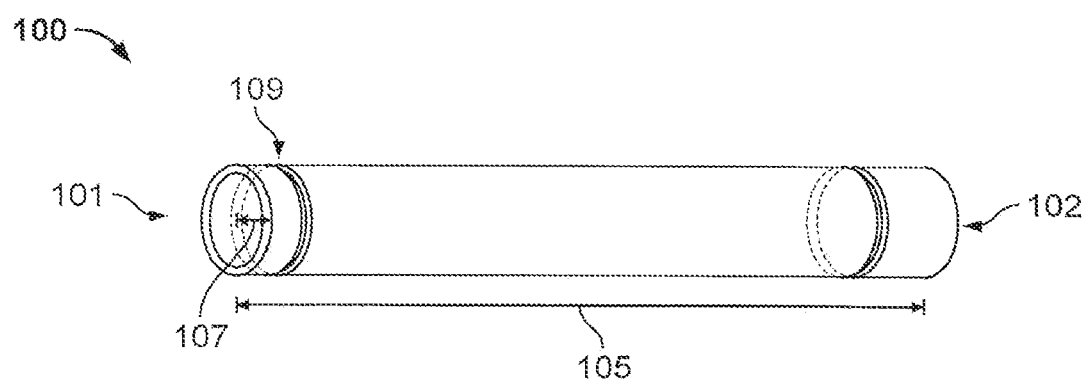
FIG. 2 illustrates an isometric view of the container body of the embodiment of the sterile packing container shown in FIG. 1.
Figure 3:
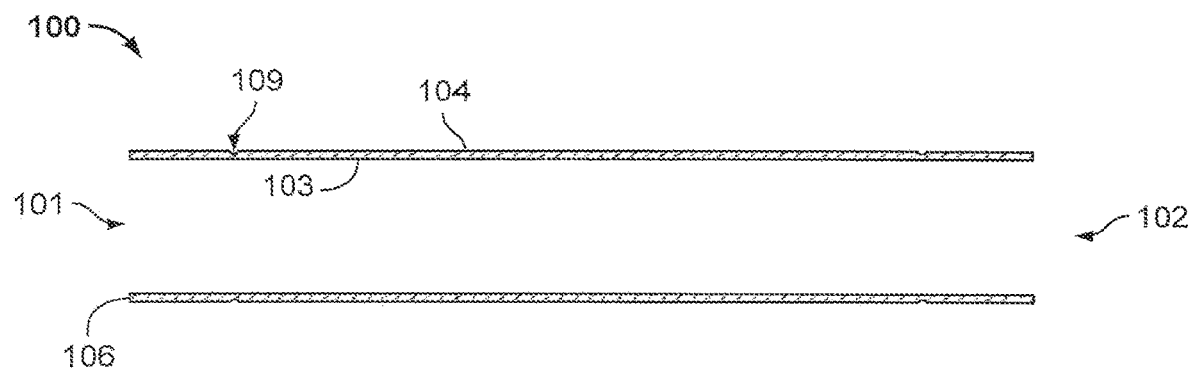
FIG. 3 illustrates a cross-sectional side view of the container body of the embodiment of the sterile packing container shown in FIG. 1.
Figure 4:
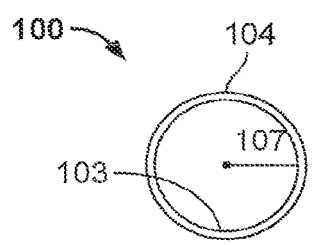
FIG. 4 illustrates a front view from the first open end of the container body of the embodiment of the sterile packing container shown in FIG. 1.

The container body 100 may be generally cylindrical with a longitudinal axis 108, a first open end 101 and a second open end 102. In the example illustrated in FIG. 2, the first open end 101 and the second open end 102 have identical radii 107. Furthermore, the cross-sectional shape of the container body 100 is constant along the majority of the length 105 of the longitudinal axis 108. The purpose of the container body 100 is to house the desired implant for delivery while maintaining the sterility of said implant. Moreover, the radius 107 of the container body 100 is constant irrespective to the length 105 of the container body 100. The radius 107 has no specific dimension, but must be sufficient to house the desired implant. Likewise, the length 105 has no specific measurement as long as the container body 100 is sufficient to house the desired implant. Lastly, the internal geometry of the container body 100 is invariant to the external geometry of the container body 100 for the length 105 of the majority of the longitudinal axis 108. Furthermore, at each the first 101 and second 102 open end is an engagement feature, such as a recess 109 that encircles the container body 100, which serves a guide for the placement of the cover 200 and closure assembly 500 upon fusion.

Figure 5:
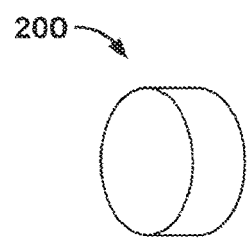
FIG. 5 illustrates an isometric view of the cover of the embodiment of the sterile packing container shown in FIG. 1.
Figure 6:
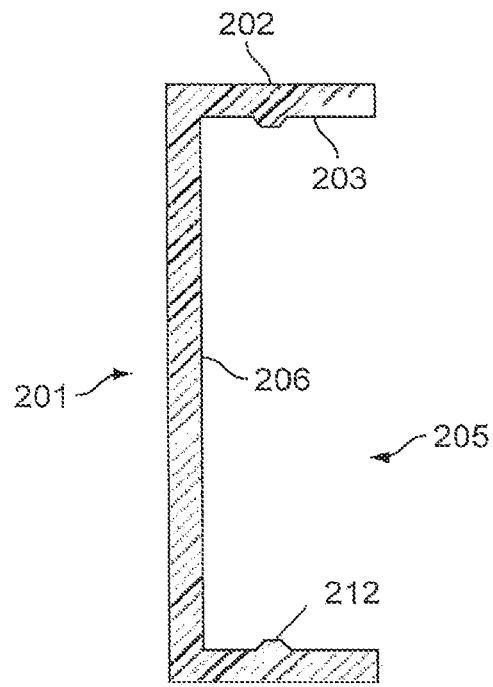
FIG. 6 illustrates a cross-sectional side view of the cover cap of the embodiment of the sterile packing container shown in FIG. 1.
Figure 7:
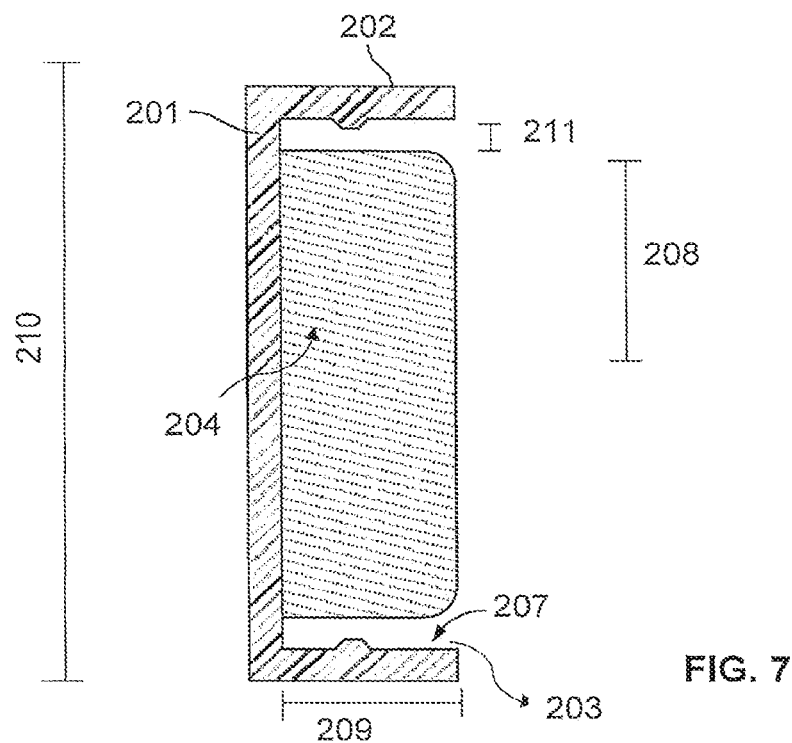
FIG. 7 illustrates a cross-sectional side view of the cover cap and stopper element of the embodiment of the sterile packing container shown in FIG. 1.

The cover 200 may be comprised of a cover cap 201 and stopper element 204. The cover 200 has no specific size or shape so long as size is sufficient to fit accordingly with the container body 100. The cover cap 201, like the cover 200, has no specific shape or size, as long as the cover cap 201 has a width 210 that exceeds the diameter 107 of the container body 100. In this embodiment, as shown in FIGS. 5-7, the cover cap 201 may be a cylinder with an aperture 205 that extends partially through the cover cap 201. Furthermore, the cover cap 201 may also include a projection 212 that forms a ring along the interior surface 203 of the cover cap 201 that engages with the recess 109 of the container body 100 on the first open end 101.

Figure 8:
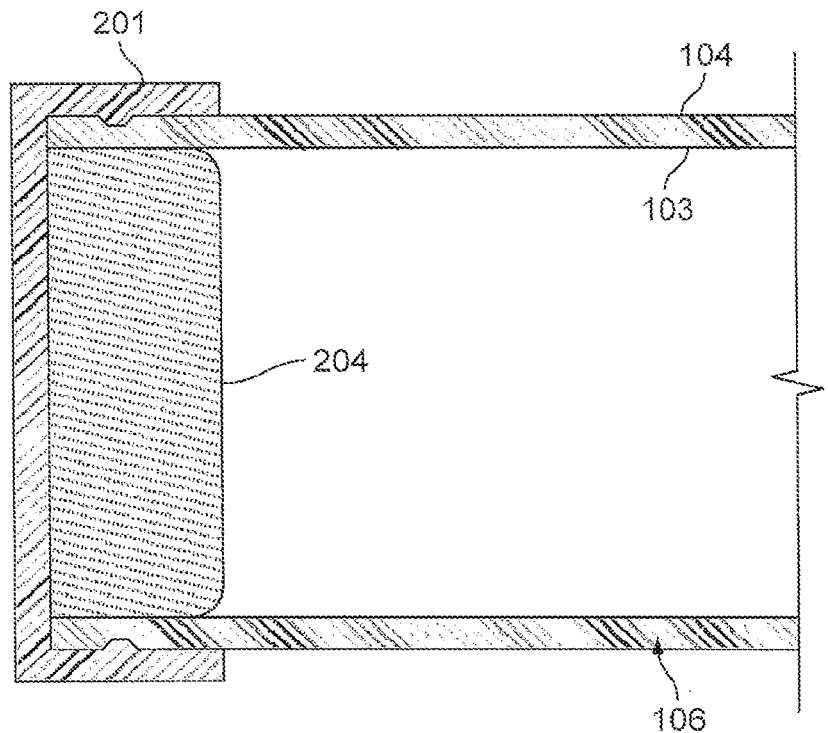
FIG. 8 illustrates a cross-sectional side view of the first open end of the container body with the cover attached thereto of the embodiment of the sterile packing container shown in FIG. 1.

The stopper element 204 has a radius 208 that is sufficient to provide a seal or barrier to the interior surface 103 of the container body 100 as shown in FIG. 8. The stopper element 204 is attached to the bottom surface 206 of the cover cap 201 and extends perpendicularly from the bottom surface 206 of the cover cap 201. The stopper element 204 has a length 209 which is the distance that it extends from the cover cap 201 and that is sufficient to adequately form the airtight seal with the interior surface 103 of the container body 100. As shown in FIG. 8, between the stopper element 204 and the interior surface 203 of the cover cap 201 is a space 207 with a width 211 that is sufficient to accept the wall 106 of the container body 100.

Figure 9:
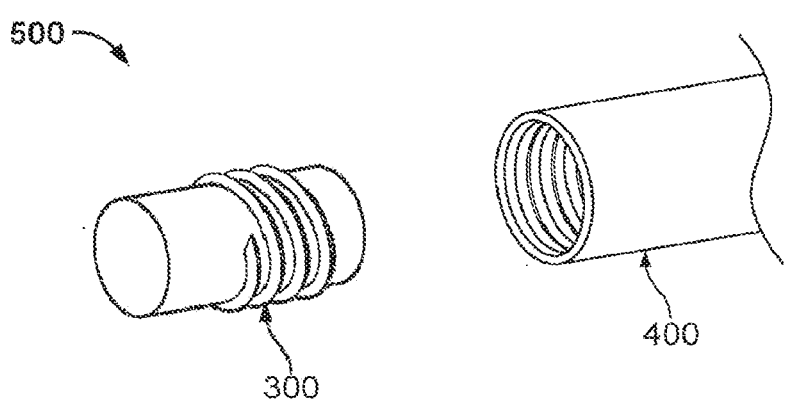
FIG. 9 illustrates an isometric view of the closure assembly of the embodiment of the sterile packing container shown in FIG. 1.
Figure 10:
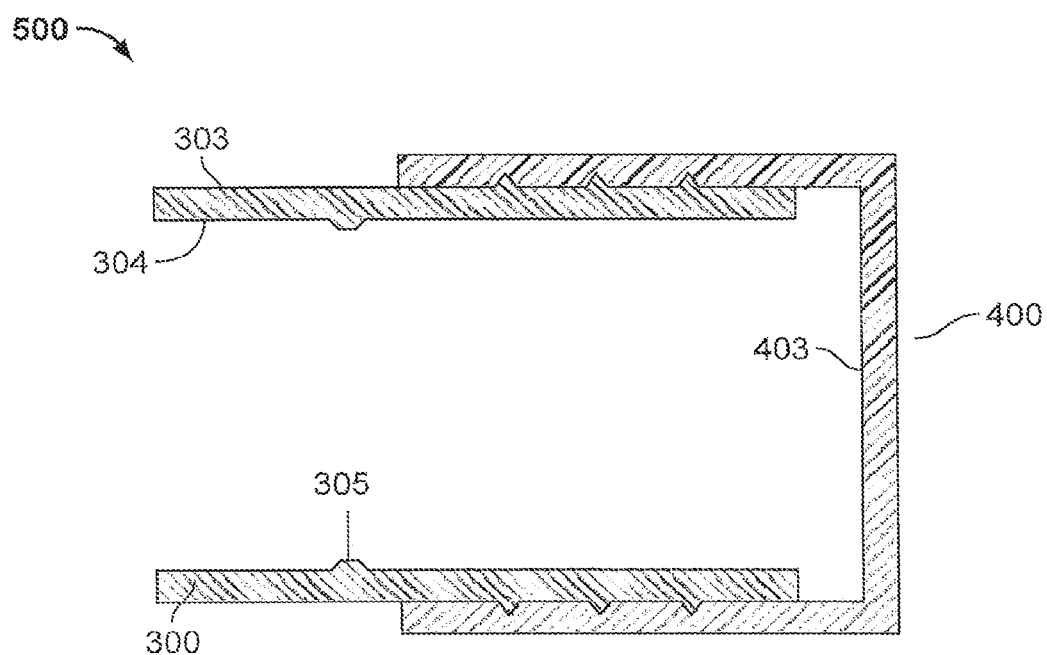
FIG. 10 illustrates a cross-sectional side view of the closure assembly of the embodiment of the sterile packing container shown in FIG. 1.
Figure 11:
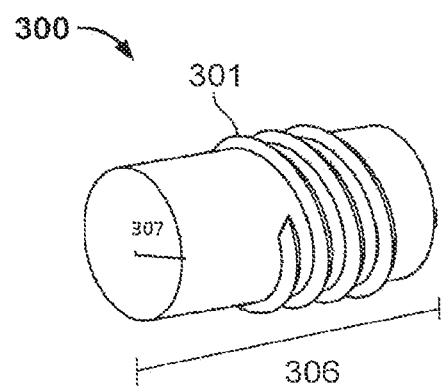
FIG. 11 illustrates an isometric view of the closure base of the embodiment of the sterile packing container shown in FIG. 1.
Figure 12:
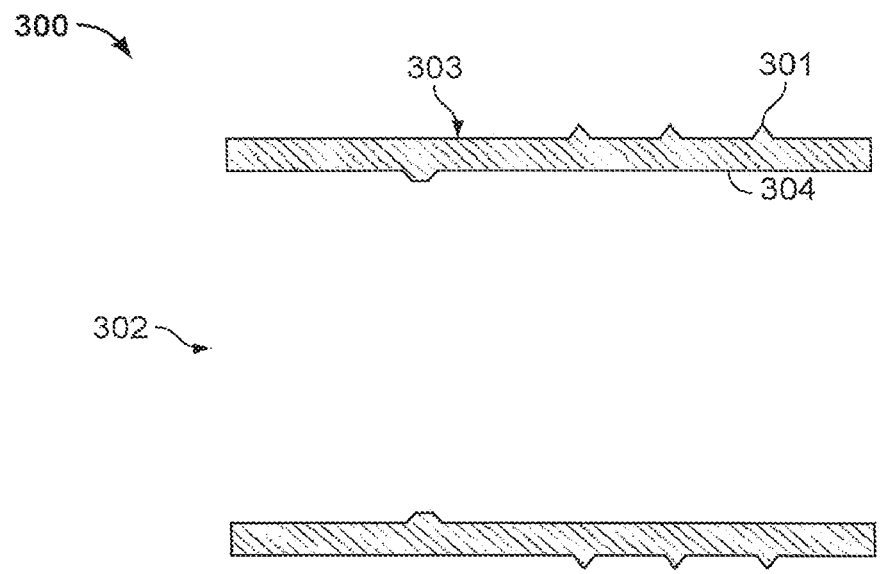
FIG. 12 illustrates a cross-sectional side view of the closure base of the embodiment of the sterile packing container shown in FIG. 1.

The sterile packaging container 1000 also includes a closure assembly 500, FIGS. 9-10. The closure assembly 500 may be comprised of a closure cap 400 and a closure base 300. The closure base 300, like the cover 200, has no specific shape or size as long the closure base 300 is large enough to encircle the second open end 102 of the container body 100. In this embodiment, as shown in FIGS. 11-12, the closure base 300 may be generally cylindrical in shape with an aperture 302 that extends the length 306 of the closure base 300, and a diameter 307 sufficient to encircle the second open end 102 of the container body 100. Located on the exterior surface 303 of the closure base 300 is a threaded portion 301 for connection to the closure cap 400. Located on the interior surface 304 of the closure base 300 is a projection 305 that forms a ring along the interior surface 304 of the closure base 300. Like the cover cap projection 212, the closure base projection 305 engages the recess 109 on the second open end 102 of the container body 100 during fusion.

Figure 13:
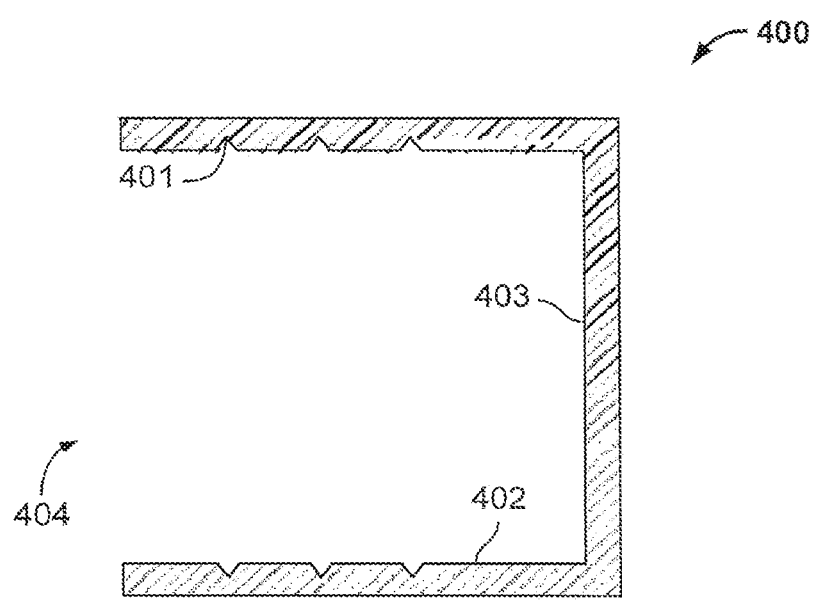
FIG. 13 illustrates a side cross-sectional view of the closure cap of the embodiment of the sterile packing container shown in FIG. 1.

Also the closure assembly 500 may include a closure cap 400, FIG. 13. The closure cap 400 has no specific shape or size as long as the closure cap 400 is large enough to encircle the closure base 300. The closure cap 400 may be generally cylindrical with an aperture 404 that extends partially through the closure cap 400 with a diameter 405 sufficient to encircle the closure base 300. The closure cap 400 may contain an internal thread 401 that is mated to the external thread 301 on the closure base 300. The threading between the closure cap 400 and closure base 300 is configured to form a microbe-tight seal that inhibits the passage of bacteria and viruses. Additionally, the seal may be an airtight (hermetic) seal.

An example of a manufacturing method of a container 1000 that comprises a closure assembly 500 with a closure cap 400 is as follows. The cover cap 201 is attached to the first open end 101 of the container body 100. The wall 106 of the container body fits between the exterior surface of the stopper element 204 and the interior surface 103 of the wall 106 of the cover cap 201. As discussed above, the stopper element 204 forms an airtight seal with the interior surface 103 of the container body wall 106. The exterior surface 104 of the container body wall 106 is hermetically sealed to the cover cap 201. The cover cap 201 is in snap fit engagement with the first open end 101.

Figure 14:
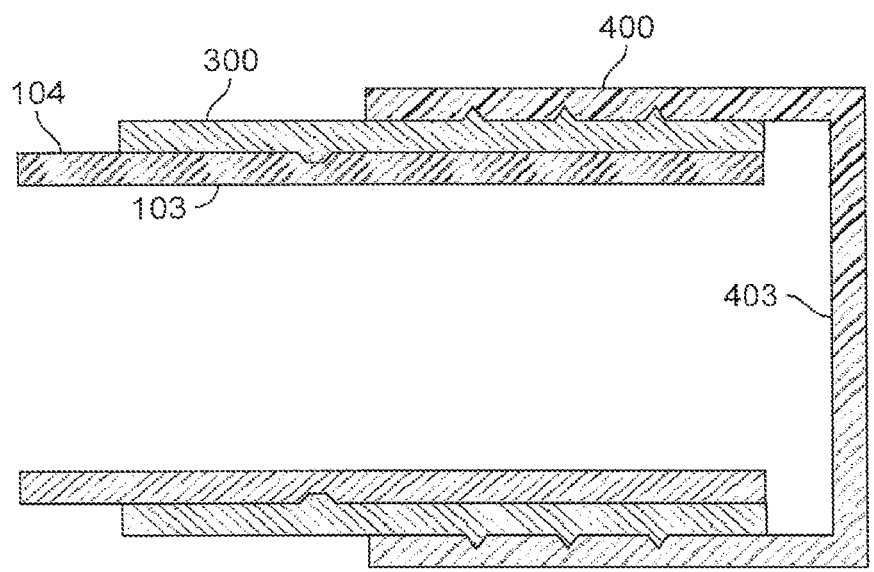
FIG. 14 illustrates a side cross-sectional view of the second open end of the container body with the closure assembly attached thereto of the embodiment of the sterile packing container shown in FIG. 1.

On the opposite end of the container body 100, at the second open end 102 the closure base 300 encircles a portion of the container body 100 forming a hermetic seal, FIG. 14. The closure cap 400 is affixed to the closure base 300 via the external threading 301 of the closure base 300 that is mated to the internal threading 401 on the closure cap 400. The closure cap 400 forms a gas permeable seal with the closure base 300 which allows for sterilization.

A method of making a sterile container is provided. The method comprises creating, by a mechanical process, a polymeric container body 100 having a first open end, a second open end, and a cross-sectional shape that is constant along the majority of the longitudinal axis. In some embodiments of the method the radius 107 is consistent throughout the length 105 of the container body 100. A polymer will be used that is acceptable for the desired method of sterilization, such as gamma or ethylene oxide sterilization. The preferred method of a manufacture is extrusion or pultrusion, although other methods could be used that produce a cross-sectional shape that is constant along the majority of the longitudinal axis 108. Either of the aforementioned methods, as opposed to injection molding or any other known method, allows the user to manufacture the container body 100 without the need of a draft profile which is often needed to remove the object from the mold, and results in a container body with an increasing radius throughout the length of the container body. The container body 100 is allowed to harden, completing the manufacture process of the container body 100.

Once the container body 100 is complete, the cover 200 is hermetically sealed to the first open end 101 of the container body 100. The cover 200 may be manufactured by various methods known in the art, such as the process of injection molding, or a similar process. The cover 200 may be affixed to the container body 100 via ultrasonic, friction welding, or other fusion welding techniques known in the art. The method involves hermetically sealing the closure base 300 to the second open end 102 of the container body 100. The closure base 300 may be manufactured via the traditional process of injection molding, or a similar process known within the art. Like the cover 200, the closure base 300 may be affixed to the container body 100 via ultrasonic, friction welding, or other fusion welding techniques known in the art. The closure cap 400 may be attached to the closure base 300 by various means. In one embodiment of the method, the cap and the base each have complementary engagement elements, such as complimentary screw threads. The threading is mated so that upon attaching the closure base 300 to the closure cap 400, the two elements form a gas permeable seal between the two that inhibits microbial entry. The sterile packaging container 1000 is sterilized by the method of gamma radiation, ethylene oxide or any other method known in the art.

Another method for the manufacturing of a sterile container comprises: extruding or pultruding a polymeric container body having a first open end, a second open end, and a cross-sectional shape that is constant along the majority of the longitudinal axis; allowing the container body to harden; sealing a cover to the first open end to create a first microbe-tight seal; sealing a closure to the second open end to create a second microbe-right seal; and sterilizing the interior of the container; wherein at least one of the first microbe-tight seal and the second microbe-tight seal is air permeable.

Figure 16:
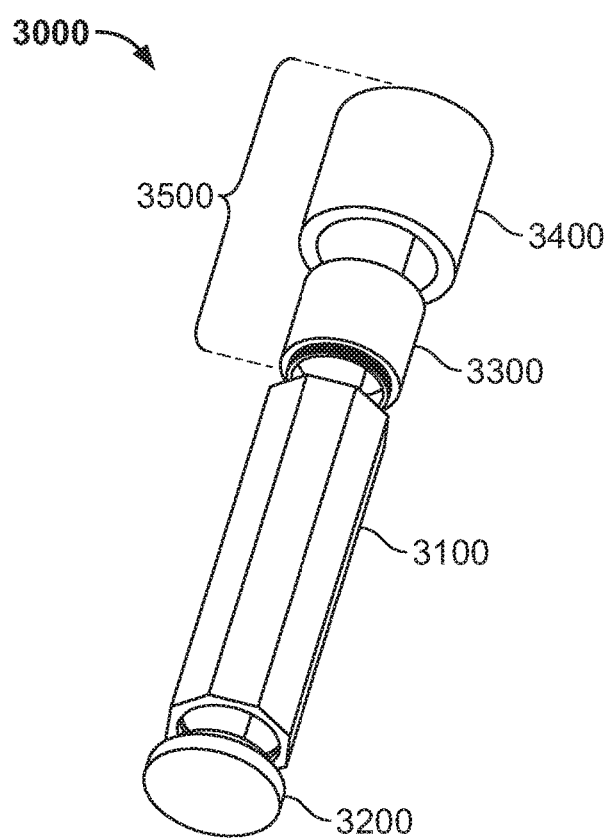
FIG. 16 illustrates a third embodiment of the sterile packaging container.

In an alternative embodiment, as shown in FIG. 16, the sterile packaging container 3000 comprises: a container body 3100, a cover 3200, and a closure assembly 3500.

Figure 18:
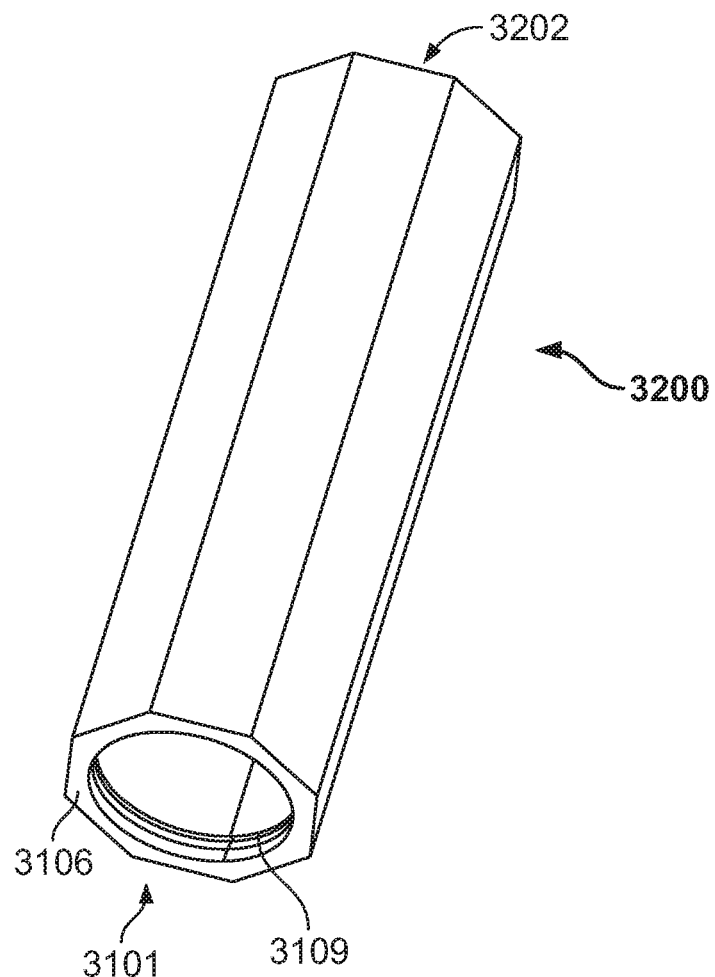
FIG. 18 illustrates an isometric view of the container body of the embodiment of the sterile packing container shown in FIG. 16.
Figure 19:
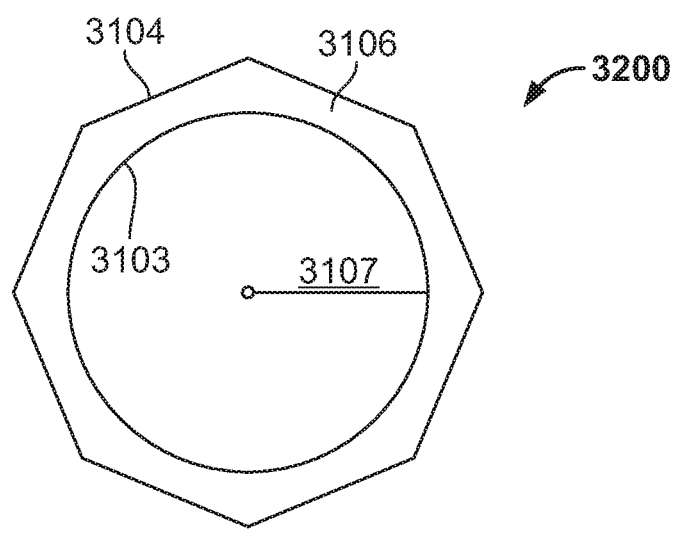
FIG. 19 illustrates a front view of the container body of the embodiment of the sterile packing container shown in FIG. 16.
Figure 20:
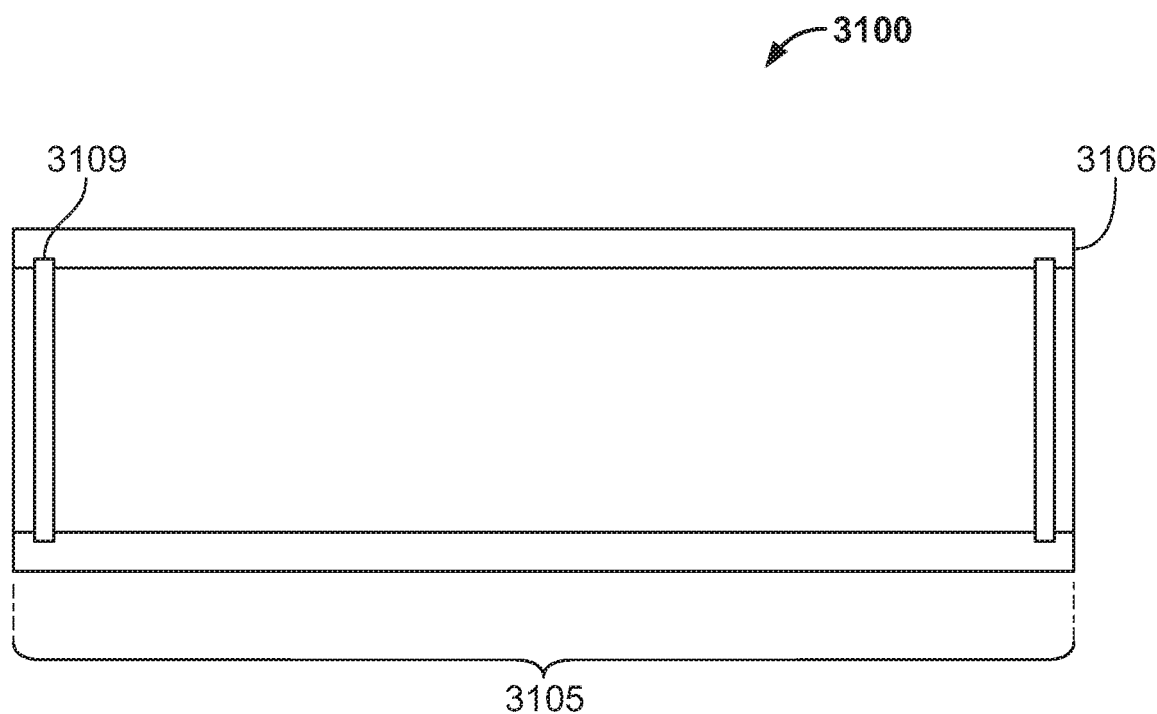
FIG. 20 illustrates a side view of the cover of the embodiment of the sterile packing container shown in FIG. 16.

The container body 3100 may be a hexagonal prism with a longitudinal axis 3108, a first open end 3101 and a second open end 3102. In the example illustrated in FIG. 17-19, the first open end 3101 and the second open end 3102 have identical radii 3107. Furthermore, the cross-sectional shape of the container body 100 is constant along the length 3105 of the longitudinal axis 3108. Furthermore, at each the first 3101 and second 3102 open end is an engagement feature, such as an internal recess 3109 that forms a ring along the interior surface 3103 the container body 3100, which serves a guide for the placement of the cover 3200 and closure assembly 3500 upon fusion.

Figure 17:
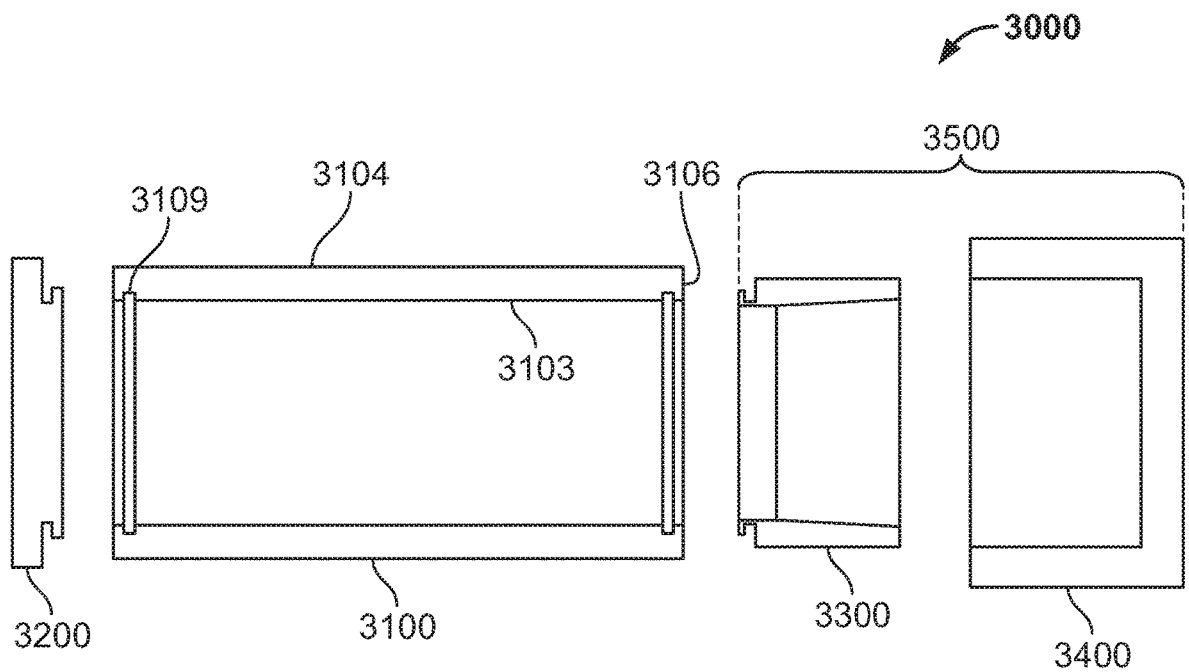
FIG. 17 illustrates a side cross-sectional view of the sterile packaging container of the embodiment shown in FIG. 16.
Figure 21:
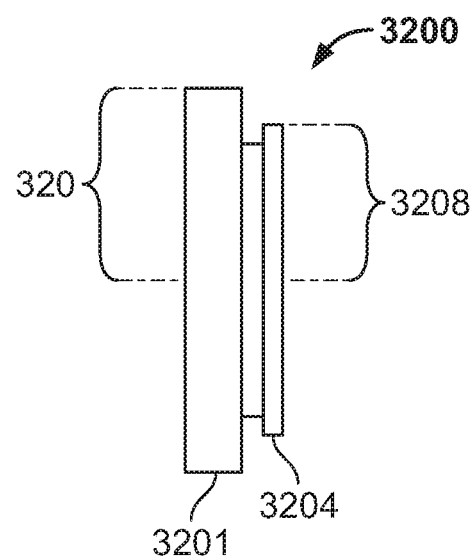
FIG. 21 illustrates a side view of the closure assembly of the embodiment of the sterile packing container shown in FIG. 16.

The cover 3200 is comprised of a cover cap 3201 and stopper element 3204, as shown in FIGS. 16, 17, and 21. The cover cap 3201, like the cover 3200, has no specific shape or size. In this embodiment, the cover cap 3201 may be a cylinder. The stopper element 3204 may generally be a cylinder with a radius 3208 that is sufficient to provide a seal or barrier to the internal recess 3109 of the container body 3100 as shown in FIG. 17. The stopper element 3204 is adjacent to the cover cap 3201 and extends horizontally from the cover cap 3201.

Figure 22:
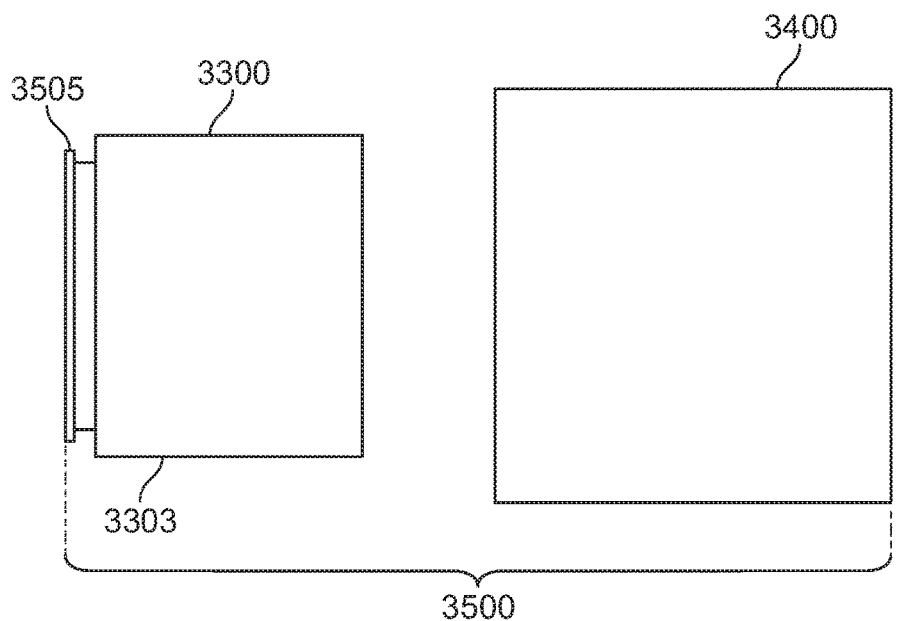
FIGS. 22 and 23 illustrate side cross-sectional views of the closure assembly of the embodiment of the sterile packaging container shown in FIG. 16.
Figure 23:
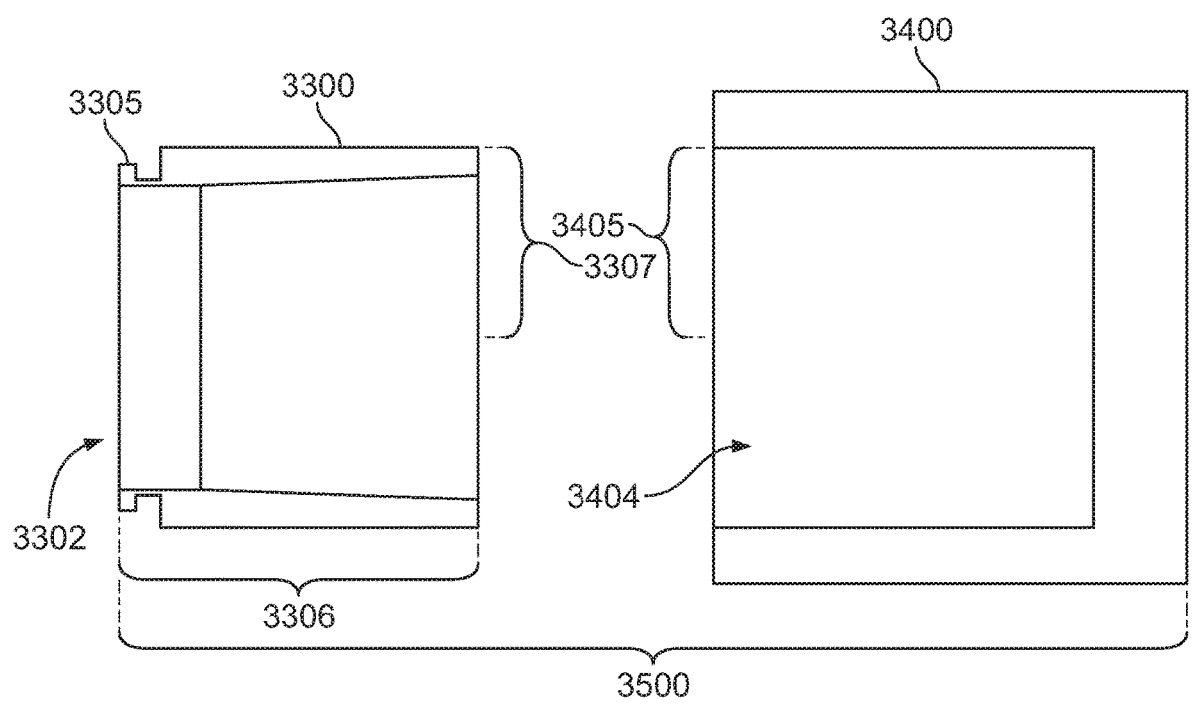

The sterile packaging container 3000 also includes a closure assembly 3500, FIGS. 22-23. The closure assembly 3500 may be comprised of a closure cap 3400 and a closure base 3300. In this embodiment, the closure base 3300, like first embodiment, has no specific shape or size, but the closure base 3300 no longer needs to encircle the second open end 3102 of the container body 3100. In this embodiment, the closure base 3300 is generally cylindrical in shape with an aperture 3302 that extends the length 3306 of the closure base 3300. Located on the exterior surface 3303 of the closure base 3300 is a projection 3305 that encircles the exterior surface 3303 of the closure base 3300. Like the stopper element described in this embodiment 3204, the closure base projection 3305 engages the internal recess 3109 on the second open end 3102 of the container body 3100 during fusion.

Also, in this embodiment, the closure assembly 3500 may include a closure cap 3400, FIGS. 16-17 and 22-23. The closure cap 3400 has no specific shape or size as long as the closure cap 3400 is large enough to encircle the closure base 3300. The closure cap 3400 may be generally cylindrical with an aperture 3404 that extends partially through the closure cap 3400 with a diameter 3405 sufficient to encircle the closure base 3300. In this embodiment, the closure cap 3400 may be affixed to the closure base 3300 via friction fit that is also configured to form a microbe-tight seal that inhibits the passage of bacteria and viruses. Additionally, the seal may be an airtight (hermetic) seal. It should be noted that the manufacture of this embodiment is identical to that of the original 1000.

Figure 15:
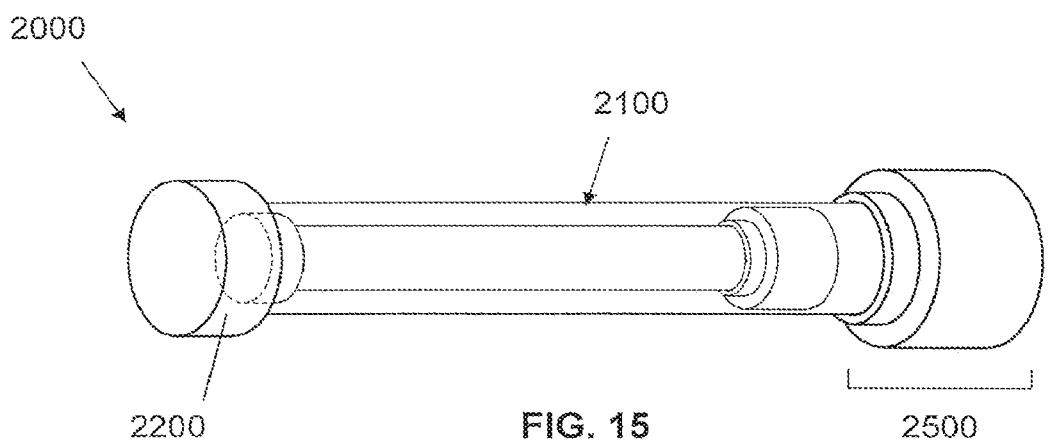
FIG. 15 illustrates a second embodiment of the sterile packaging container.

Additional embodiments of the present disclosure describe a sterile packaging container 2000 that is configured to allow for the external sterilization of a similar sterile packaging container 1000. The sterile packaging container 2000 as illustrated in FIG. 15 comprises: a second container body 2100, a second cover 2200, and a second closure assembly 2500.

The configuration and manufacture of this embodiment is identical to that of the original 1000. However, the dimensions are dependent on the varying size of the original sterile packaging container 1000. For example, the container body, while still having a longitudinal axis, a first open end, and a second open end, wherein the container body has a cross-sectional shape that is uniform along the entire length of the longitudinal axis, now has a radius that must exceed the radii of the cover 200 and closure assembly 500 of the first sterile packaging container 1000. As such, the remaining elements, like the first sterile packaging container 1000, must be dimensioned to accommodate the container body 2100. However, in this particular embodiment, the first sterile packaging container 1000, is placed within the container body 2100. Upon placement within the second container body 2100, and the assembly of the remaining elements, the sterile packaging container 2000, and the exterior of the first sterile packaging container 1000 is sterilized using by the method of gamma radiation, ethylene oxide or any other method known in the art.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A container configured for sterilization and gas permeation, the container comprising:
   a container body with a longitudinal axis, a first open end, and a second open end, wherein the container body has a cross-sectional shape that is constant along the majority of the longitudinal axis;
   a cover comprising a cover cap and a stopper element, the cover forming a microbe-tight seal on the first open end; and
   a closure assembly that forms a microbe-tight seal on the second open end, said closure assembly comprising a closure base attached to the container body at the second open end, and a closure cap removably engaged to the closure base.

2. The container of claim 1, wherein the external and internal cross-sectional contours of the container body are invariant to one another along a majority of the longitudinal axis.

3. The container of claim 1, wherein the container body is the product of polymer extrusion.

4. The container of claim 1, wherein the container body is the product of polymer pultrusion.

5. The container of claim 1, wherein the stopper element is in a plug engagement with the first open end.

6. The container of claim 1, wherein the cover forms a hermetic seal with the first open end.

7. The container of claim 1, wherein the closure base is generally cylindrical with an aperture, and an exterior threaded portion configured to engage the closure cap.

8. The container of claim 7, wherein the closure cap comprises an internal threaded portion engaged to the exterior threaded portion of the closure base.

9. The container of claim 1, wherein the closure base and the closure cap form a breathable seal configured to inhibit the passage of bacteria.

10. The container of claim 9, wherein the breathable seal is configured to inhibit the passage of viruses.

11. The container of claim 1, comprising a sterile internal volume that is bounded by the container body, the cover, and the closure.

12. The container of claim 1, wherein said container is constructed of a material that is suitable for sterilization by at least one of: gamma radiation and ethylene oxide.

* * * * *